United States Patent [19]

Goldenberg

[11] Patent Number: 4,460,561
[45] Date of Patent: * Jul. 17, 1984

[54] TUMOR LOCALIZATION AND THERAPY WITH LABELED ANTIBODIES SPECIFIC TO INTRACELLULAR TUMOR-ASSOCIATED MARKERS

[76] Inventor: M. David Goldenberg, 636 Lakeshore Dr., Lexington, Ky. 40502

[*] Notice: The portion of the term of this patent subsequent to Nov. 30, 1999 has been disclaimed.

[21] Appl. No.: 415,876

[22] Filed: Sep. 8, 1982

Related U.S. Application Data

[63] Continuation-in-part of Ser. No. 126,261, Mar. 3, 1980, Pat. No. 4,361,544.

[51] Int. Cl.$^3$ .................. A61K 43/00; A61K 49/00
[52] U.S. Cl. ........................... 424/1.1; 260/112 R; 260/112 B; 424/9
[58] Field of Search ............ 424/1, 9; 260/112 R, 260/112 B

[56] References Cited

U.S. PATENT DOCUMENTS

| | | | |
|---|---|---|---|
| 3,927,193 | 12/1975 | Hansen et al. | 424/1 |
| 3,960,827 | 6/1976 | Björklund | 424/12 |
| 4,144,031 | 3/1979 | Acevedo et al. | 23/230 B |
| 4,146,603 | 3/1979 | Davidson et al. | 424/12 |
| 4,160,019 | 7/1979 | Björklund | 424/12 |
| 4,174,385 | 11/1979 | Reid | 424/12 |

FOREIGN PATENT DOCUMENTS 5638 11/1979 European Pat. Off. ................ 424/1

OTHER PUBLICATIONS

Mach et al., Eur. J. Cancer, Suppl. 1, 113, (1978).
Spar, Sem. Null. Mfd., 6, (1976), 379.
Emrich, Dstch. Mtd. Wschr., 104, 153, (1979).
Lee et al., Scand. J. Immunol., 8, (Suppl. 8), 485, (1978).
Heyderman, Scand. J. Immunol., 8, (Suppl. 8), 119, (1978).
Goldenberg et al., N. Eng. J. Med., 298, 1384, (1978).
Hawthorne et al., J. Med. Chem., 15, 449, (1972).
Order, Radiology, 118, 219, (1976).
Ettinger et al., Cancer Treat. Rep., 63, 131, (1979).
Order et al., Int. J. Rad. Oncology. Biol. Phys., 6, 703, (1980).
Quinones et al., J. Null. Med., 12, 69, (1971).
Hirai et al., Abst. 6th Int. Res. Group Carc. Proteins, Sep. 17-21, 1978, p. 14.
Yoshimoto et al., Am. J. Obstet. Gynocol., 134, 729, (1979).
Begent et al., J. Royal. Soc. Med., 73, 624, (1980).
Balg et al., Cancer Res., 40, 2965, (1980).
Gold et al., Cancer Res., 40, 2973, (1980).
Koji et al., Cancer Res., 40, 3013, (1980).
Bagshawe et al., Cancer Res., 40, 3016, (1980).
Order et al., Cancer Res., 40, 3001, (1980).
Ghose et al., Cancer Res., 40, 3018, (1980).
Papsidero et al., Cancer Res., 40, 3032, (1980).
McIntire, Cancer Res., 40, 3083, (1980).
Ballou et al., Science, 206, 844, (1979).

*Primary Examiner*—Christine M. Nucker
*Attorney, Agent, or Firm*—Millen & White

[57] ABSTRACT

Methods are provided for using radiolabeled antibodies specific to intracellular tumor-associated markers for detection, localization and therapy of tumors. Injectable compositions for use in the methods of the invention are also provided.

17 Claims, No Drawings

TUMOR LOCALIZATION AND THERAPY WITH LABELED ANTIBODIES SPECIFIC TO INTRACELLULAR TUMOR-ASSOCIATED MARKERS

CROSS REFERENCE TO RELATED APPLICATIONS

This application is a continuation-in-part of copending application U.S. Ser. No. 126,261, filed Mar. 3, 1980, now U.S. Pat. No. 4,361,544, the disclosure of which is incorporated herein by reference.

BACKGROUND OF THE INVENTION

U.S. Pat. No. 3,927,193 to Hansen et al discloses a method of tumor localization using labeled antibodies to carcinoembronic antigen (CEA), but provides examples of its use only in animals. Goldenberg et al, *New Eng. J. Med.*, 298, 1384 (1978), reported success in clinical trials of tumor detection and localization by scintillation scanning of patients receiving radiolabeled antibodies to CEA. A special scanner subtraction technique with other radionuclides to compensate for interstitial and blood-pool background activity was considered essential for unequivocal tumor localization using that method.

However, CEA is considered to be primarily a cell-surface antigen, as reported by Heyderman, *Scand. J. Immunol.*, 8, Suppl. 8, 119 (1978), and many others. It had been thought that tumor localization in man using injected radiolabeled tumor-associated antigens required antibodies which were specific to antigens located on the surface of the tumor cell, by Spar, *Seminars In Nucl. Med.*, 6, 379 (1976) and Emrich, *Deutsche Med. Woch.*, 104, 153 (1979). It is known tha both human chorionic gonadotropin (HCG) and alpha-fetoprotein (AFP) are cytoplasmic intracellular tumor-associated substances, Heyderman, Supra, Lee et al, Guillouzo et al, Albrechtsen et al and Ruoslahti et al, in *Scand. J. Immunol.*, 8, Suppl. 8, pp. 485ff, 289ff, 165ff and 3ff, respectively (1978). Quinones et al, *J. Nucl. Med.*, 12, 69 (1971) demonstrated that a human choriocarcinoma grown in hamsters could show a 2.8-fold increased uptake of radiolabeled anti-HCG antibody in the tumor as compared to that in the animals' liver. Hirai et al, *Abstracts 6th Int. Res. Group for Carcinoembryonic Proteins*, Marburg/Lahn, Fed. Rep. of Germany, Sept. 17–21, 1978, reported that administration of radiolabeled anti-AFP antibodies to rodents with transplanted human hepatoma, and with rat and human yolk sac tumors, revealed no "homing in" of the antibody in the tumor tissues. Tumor radiotherapy using labeled antibodies has been suggested by many, and an indication of its success in a single multimodal therapeutic clinical use is reported by Ettinger, *Cancer Treat Rep*, 63, 131 (1979). The use of boron-labeled antibodies in therapy is reported by Hawthorne et al., *J. Med. Chem.*, 15, 449 (1972), but the combined incorporation of boron and a radioisotope for localization is not suggested.

A need continues to exist for a method of tumor detection and localization which is not confined to the use of antibodies to cell-surface antigens, which does not require repeated injections of background-compensating material for a subtraction technique, which is adaptable to both diagnosis and therapy, and which has a high reliability and a high resolution.

OBJECTS OF THE INVENTION

Accordingly, it is an object of the present invention to provide a method of tumor localization and detection which achieves high resolution and which uses antibodies to intracellular tumor-associated marker substances.

A further object of this invention is to provide a method of tumor therapy wherein thermal neutrons excite a boron-10 isotope-containing antibody which has been localized by detection of an attached radioisotope label.

Upon further study of the specification and appended claims, further objects and advantages of this invention will become apparent to those skilled in the art.

SUMMARY OF THE INVENTION

The foregoing objects are achieved by providing a method for detecting and localizing a tumor which either produces or is associated with an intracellular marker substance, which comprises injecting a human subject parenterally with an antibody specific to said marker substance and radiolabeled with a pharmacologically inert radioisotope capable of detection using a photoscanning device, and with indifferent immunoglobulin from the same or different species as that used to prepare said specific antibody, said indifferent immunoglobulin being radiolabelled with a pharmacologically inert radioisotope of a different element from that used to label the specific antibody and emitting at an energy capable of independent detection using said photoscanning device, the radiolabeling be so effected that the kinetics and distribution of the radiolabeled specific antibody and indifferent immunoglobulin in said subject are substantially the same during the time period required for scanning; and scanning the subject with said photoscanning device, the level of activity of the labeled indifferent immunoglobulin being used to determine the distribution of background activity due to non-targeted specific antibody, said background activity being subtracted from the total activity of specific antibody, whereby the activity of substantially only the targeted tumor-localized specific antibody is determined and said tumor is thereby detected and localized.

DETAILED DISCUSSION

The antibodies used in the present invention are specific to a variety of intracellular tumor-associated antigens as marker substances. These markers may be substances produced by the tumor or may be substances which accumulate within tumor cells, whether in the cytoplasm, the nucleus or in various organelles or subcellular structures. Among such tumor-associated markers are those disclosed by Herberman, "Immunodiagnosis of Cancer", in Fleisher, ed., "The Clinical Biochemistry of Cancer", page 347 (American Association of Clinical Chemists, 1979) and in U.S. Pat. No. 4,150,149 to Wolfsen et al.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-subunit (HCG-beta), colon-specific antigen-p (CSAp), prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, galactosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF).

Marker-specific antibodies may be produced by conventional methods well known in the art. Normally, an animal, preferably a rodent, a rabbit or more preferably a goat or primate is challenged with a tumor-associated marker substance, to which its immune system reacts by producing specific antibodies to these markers. The animal is bled, the immunoglobulin fraction of the blood is isolated, and the specific immunoglobulin isolated by a variety of conventional separation techniques, preferably including one or more affinity chromotography purification steps. Suitable such general methods for raising antibodies specific to tumor-associated marker substances are disclosed inter alia in "Immunodiagnosis of Cancer", Herberman et al, Eds. (Marcel Dekker, Inc., New York and Basel, 1979) and "Cancer Markers", Sell, Ed. (Humana Press, Clifton, N.J. 1980).

Antibodies produced by the foregoing conventional techniques are normally mixtures of antibodies a certain proportion of which are specific but generally containing a small proportion of antibodies which are cross-reactive with non-tumor-associated antigens. Antibodies purified by repeated affinity chromatography using bound antigens with which some components of the antibody mixture are cross-reactive, as well as passage through a column containing bound purified antigen, have a high specific immunoreactivity; often approaching or even exceeding 70%, and a cross-reactivity with non-tumor associated antigens of less than 15%. These antibodies are considered substantially monospecific to the antigen to which they have been raised, and are preferably used in the present invention.

Highly specific monoclonal antibodies can also be produced by hybridization techniques. Such antibodies normally require little or no purification and normally have a specific immunoreactivity of at least 85%, with specificities of more than 95% in certain cases. Such monoclonal, hybridoma-derived antibodies are also preferred for use in the present invention. In a preferred embodiment, monoclonal antibodies are produced by challenging a monkey with an intracellular tumor-associated marker, fusing antibody-producing monkey lymph or spleen cells with human or mouse myeloma cells to produce hybrid cells which are then isolated, cloned and selected for their ability to produce monoclonal antibodies specific to said marker substance.

Monoclonal antibodies from the immunoglobulin G (IgG) fraction are obtained by the present method, and are used to prepare the compounds used for tumors detection, localization and therapy according to this invention. The IgM monoclonal antibodies of Koprowski, U.S. Pat. No. 4,172,124, are unsuitable for use in the present method.

Antibodies may be labeled by any of several techniques known to the art. A wide range of labeling techniques are disclosed in Feteanu "Labeled Antibodies in Biology and Medicine", pages 214-309 (McGraw-Hill Int. Book Co., New York, et al 1978). The introduction of various metal radioisotopes may be accomplished according to the procedures of Wagner et al., *J. Nucl. Med.*, 20, 428 (1979); Sundberg et al., *J. Med. Chem.*, 17, 1304 (1974); and Saha et al, *J. Nucl. Med.*, 6, 542 (1976). The foregoing are merely illustrative of the many methods of radiolabeling proteins known to the art.

Among the radioisotopes used, gamma-emitters, positron-emitters, x-ray-emittes and fluorescence-emitters are suitable for localization and/or therapy, while beta-emitters and alpha-emitters may also be used for therapy. Suitable radioisotopes for labeling antibodies include Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Scandium-47, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism. Preferably the radioisotope will emit in the 10-5,000 kev range, more preferably 100-500 kev.

A preferred labelling technique involves labeling with either Iodine-131 (I-131) or Iodine-123 (I-123) using an oxidative procedure wherein a mixture of radioactive potassium or sodium iodide and the antibody is treated with chloramine-T, e.g., as reported by Greenwood et al, *Biochem. J.*, 89, 114 (1963) and modified by McConahey et al, *Int. Arch. Allergy Appln. Immunol.*, 29, 185 (1969). This results in direct substitution of iodine atoms for hydrogen atoms on the antibody molecule, presumably on tyrosine residues, possibly also on tryptophane and even on phenylalanine residues, depending on the proportions of reagents and the reaction conditions.

In general, it is desirable to introduce as high a proportion of radiolabel as possible into the antibody molecule without destroying its immunospecificity. For example, while the vast majority of investigators had considered that introduction by direct substitution of more than from 1.5 to 2 iodine atoms per antibody molecule is disadvantageous, it has now been found that the introduction by direct substitution of at least 2.5 and preferably an average of from 5 to 10 iodine atoms per antibody molecule is advantageous. This is especially the case where the antibody is highly marker-specific, e.g., having a marker specific immunoreactivity of at least 70%, preferably at least 80%, and a cross-reactivity of less than 15%, preferably less than 10%, prior to labeling. In this case, even a reduction of the antibody specificity of from 5 to 33% as a consequence of high labeling is outweighed by the advantage of high activity, permitting the use of substantially smaller quantities of labeled antibody. As noted above, the use of highly specific antibodies of high activity results in efficient localization and increased resolution. This balancing of increased activity with reduced specificity is advantageous with up to an average of 10 atoms of iodine per antibody molecule after which the reduction in specificity outweighs the advantage of high activity. Using other methods for the introduction of radiolabel, it may be possible to further increase the proportion of label to antibody without paying an unacceptable price in reduced immunospecificity. A further improvement may be achieved by effecting radiolabeling in the presence of the specific antigen, to insure that the antigen binding site on the antibody will be protected. The antigen is separated after labeling.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography, and scandium-47 (and other alpha-emitting radionuclides) are preferable for tumor therapy.

A useful method of labeling antibodies with such radiometals is by means of a bifunctional chelating agent, such as diethylenetriaminepentaacetic acid (DTPA), as described, for example, by Khaw et al. (Science 209, 295, 1980) for In-111 and Tc-99m, and later by Scheinberg et al. (Science 215, 1511, 1982). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33, 327, 1982) for labeling of albumin with In-111, but which can be adapted for labeling of antibodies. A suitable method of labeling antibodies with Tc-99m which does not use chelation with DPTA is the pretinning method of Crockford et al., U.S. Pat. No. 4,323,546; also described in "Tumor Imaging. The Radiochemical Detection of Cancer," Burchiel et al., Eds, pp. 111–123 (Masson Publishing USA, New York, 1982).

A preferred method of labeling immunoglobulins with Tc-99m is that described by Wong et al. in Int. J. Appl. Radiat. Isot., 29, 251 (1978) for plasma protein, and recently applied successfully by Wong et al. in J. Nucl. Med., 23, 229, 1981 for labeling antibodies.

In the case of the radiometals conjugated to the specific antibody, it is likewise desirable to introduce as high a proportion of the radiolabel as possible into the antibody molecule without destroying its immunospecificity. Again, even a reduction of the antibody specificity of from 5 to 33% as a consequence of high labeling is outweighed by the advantage of high specific activity, permitting the use of substantially smaller quantities of the labeled antibody and/or effecting a higher sensitivity of the tumor-locating method, on the one hand, or a more effective antitumor therapy, on the other. This reduction in immunospecificity of the highly purified or monoclonal antibody, however, should not so affect the preparation as to alter its in vivo biodistribution and metabolism such that the principle of subtraction of the radioactivity of the indifferent immunoglobulin from that of the similarly distributed (with the exception of accretion in the tumor) antitumor antibody is compromised. A further improvement may be achieved by effecting radiolabeling in the presence of the specific antigen, to insure that the antigen binding site on the antibody will be protected. The antigen is separated after labeling.

The foregoing are merely illustrative of the many methods of radiolabeling proteins known to the art. These procedures can also be used in a substantially identical manner for labeling irrelevant (indifferent) immunoglobulin of the same or a different species as that of the antitumor antibody in order to effect the subtraction process disclosed herein for imaging neoplasms.

A further aspect of the present invention relates to the use of antibodies containing both a radioisotope label and an addend containing significant numbers of boron atoms, having at least the 20% natural abundance of boron-10 isotope. The boron-containing addend may be introduced by a variety of methods, preferably by coupling the antibody with a boron-rich coupling agent, such as the diazonium ion derived from 1-(4-aminophenyl)-1,2-dicarbacloso-dodecaborane(12), according to the method of Hawthorne et al, J. Med. Chem., 15, 449 (1972). The boron-10-containing antibody is then radiolabeled according to one or more of the above procedures to produce an antibody containing both one or more radiolabels for tumor localization and/or therapy and a high content of boron-10 atoms for the absorption of thermal neutrons. Boron-10 absorbs thermal neutrons and the activated nucleus decays rapidly to Lithium-7 and an alpha-particle. These resultant alpha-particles are cytotoxic, and their production in tumor cells kills the cells and causes tumor reduction.

Combination of a boron addend with one or more radiolabels on a highly marker-specific antibody provides for the first time a single agent which functions as a multimodal tumor therapeutic agent. The rapid and specific localization of these doubly labeled antibodies at the site of a tumor by any of the techniques of this invention including subtraction using labeled indifferent immunoglobulin, permits a rapid and precise definition of the areas where neutron irradiation should be focused. Moreover, as tumor cells are destroyed by the combined effects of radiation from the radiolabel and neutron-activated boron-10 emissions, and the killed tumor cells are eliminated, the progress of the radiotherapeutic treatment may be monitored by measurement of the rate of decrease in localized, radiolabeled antibody or other tumor detection method.

Mixtures of labeled antibodies specific to antigens associated with the same or different tumor or tumor cell types may be used. This can enhance detection, localization and/or therapy in certain cases, and can also increase the range of a broad screen for more than one tumor or tumor cell type.

Radioactivity due to accumulation of labeled antibody or its metabolites in the blood-pool or in interstitial fluids can significantly reduce the resolution of tumor localization using labeled antibodies specific to tumor-associated markers. In such cases, it is advantageous to inject a reference substance into the subject prior to photoscanning, the reference substance being radiolabeled with a radioisotope emitting at a different energy from the marker specific antibody label and capable of independent detection by the photoscanning device. The level of activity of the reference substance is used to determine the background activity due to non-targeted specific antibody, this background activity is then subtracted from the total activity of the specific antibody permitting a determination of the activity of substantially only the targeted, tumor-associated antibody. It is known to use technetium-99m-labeled substances for a determination of blood pool and interstitial background activity, as disclosed in Goldenberg et al, *New Eng. J. Med.*, 298, 1348 (1978). That reference discloses the use of Tc-99m-labeled human serum and Tc-99m-pertechnetate. Separate injection of these reference substances was necessary prior to each photoscan.

The present invention includes the use of Tc-99m-labeled normal immunoglobulin and Tc-99m-labeled sulfur colloid among suitable reference substances. Preferably, however, the reference substance is normal, indifferent immunoglobulin from the same or different species as that used to prepare the specific antibody used as the tumor localization agent. This normal immunoglobulin is preferably radiolabeled with a different isotope of the same element used to label the specific antibody, and is preferably injected concurrently with the radiolabeled marker-specific antibody. This has the advantage of using as a reference substance a molecular species having essentially the same kinetics of binding, distribution and metabolism as the labeled specific antibody. As a consequence, only a single injection of the reference substance is necessary, and increased resolution is achieved.

Suitable such pairs of radioisotopes, one of which may be used for labeling the specific antibody and the other of which is used to label the normal immunoglobulin include Iodine-131 and Iodine-123; Indium-111 and Indium-113m; Gallium-67 and Gallium-68; Ruthenium-97 and Ruthenium-103; or Mercury-197 and Mercury-203. Because iodine may be introduced directly by a chemical substitution reaction, and has at least three isotopes which are radioactive and detectable using a photoscanning device, iodine is preferred for radiolabeling both the specific antibody and the normal immunoglobulin reference substance for use in the method of the invention. Advantageously, Iodine-131 is used for labeling the specific antibody and Iodine-123 is used for labeling the normal immunoglobulin.

Critical to the method of computer-assisted subtraction for more precise tumor imaging by an external radiation detection machine is the substantially similar distribution in the body of the antitumor antibody labeled with one isotope to that of the indifferent immunoglobulin labeled with an isotope of a different energy capable of separate identification by the radiation detection camera and thus permitting the latter to be subtracted from the former. However, the second radionuclide need not be of the same element (such as I-123 for the indifferent immunoglobulin and I-131 for the antitumor antibody). For example, the antitumor antibody may be labeled with I-131 and the indifferent immunoglobulin with Tc-99m, In-111, or Ga-67; the antitumor antibody may be labeled with In-111 and the indifferent immunoglobulin with Tc-99m; or variations thereof.

The choice of the combination of radionuclides used is determined not only by the imaging qualities of said radionuclides, but further by the stability, chemical and biological integrity, and biodistribution properties of the diversely radiolabeled antibody and immunoglobulin preparations. These can be determined, for example, by assessing the immunoreactivity of the antibody and the antigenicity of the indifferent immunoglobulin by binding properties to the appropriate tumor antigen or antiimmunoglobulin antibody, respectively, these being bound to an affinity column, for example, as described in U.S. Ser. No. 126,261 for I-131 or I-123-labeled antibodies to CSAp. The physicochemical integrity of the labeled immunoglobulins can be confirmed by protein electrophoresis or gel filtration procedures, which should show that the majority of the immunoglobulin electrophoreses or chromatographs with the radiolabel.

Finally, and perhaps most important, both labeled preparations, when injected in animals in equivalent amounts of immunoglobulin protein or in amounts reflecting the ratios by which they will be injected in humans, will have similar or virtually identical organ distribution during the period after injection when imaging is to be undertaken, which in humans is up to about 48 hours, preferably less than 24 hours. It has been shown, for example, by Hnatowich et al., *Int. J. Appl. Radiat. Isot.*, 33, 327 1982 that albumin labeled with In-111 using the chemically coupled ligand diethylenetriaminepentaacetic acid (DTPA) has a substantially similar biodistribution in normal mice at 45 min after injection to albumin labeled with I-125. These three approaches to confirming the integrity and biokinetic similarity of the differently labeled preparations are meant as examples and are not restrictive of methods available for such purposes to one skilled in this technology.

The isotopes used to label the immunoglobulins and the method of this conjugation are only important in this process to the degree that they do not affect the physicochemical and biological properties of said immunoglobulins, as illustrated above, and thus hinder their similarity in biodistribution (kinetics, clearance, etc.) after injection and during the time frame when imaging is desired (which is also determined by the isotopes' half-lives).

Among the significant advantages of using as a reference substance a molecular species having essentially the same kinetics of binding, distribution and metabolism as the labeled specific antibody are that only a single injection of the reference substance is necessary, increased resolution is achieved, and tumor localization can be achieved in a shorter time. The reference substance in the present method is the corresponding indifferent immunoglobulin G (IgG) from the same or different species as that used to prepare the specific antibody used as the tumor localization agent. The indifferent IgG is radiolabeled with a different radioisotope from that used to label the specific antibody, and which is capable of independent scintigraphic detection. The labeling is so effected that the resultant labeled specific antibody and indifferent IgG have substantially the same kinetics and distribution in the patient during the time period required for scintigraphic scanning and tumor localization.

Further improvement in resolution is achieved by using a highly purified radiolabeled indifferent IgG for the reference substance in the subtraction technique. Normal globulin is a mixture of globulins, some of which may bind to the specific antigen to which the radioactive antibody is directed. Therefore, it is desirable to purify the normal globulin to be used as a subtraction agent so as to remove any reactivity to the specific marker in question, and one such purification method is to adsorb the normal immunoglobulin with the specific antigen, preferably on a solid adsorbent, so that the globulins reacting with the antigen will be retained on the column and the materials passing through will be more suitable for labeling as a nonspecific subtraction agent. Monoclonal non-specific immunoglobulin or myeloma protein itself will also have the desired purity for labeling and use as subtraction agents.

The resultant emissions are separately detectable on two different channels of a gamma-scintillation detector. The resultant scanning data are conveniently stored in a minicomputer and the aforementioned subtraction procedure is effected to determine the regions of excess accumulation of radiolabeled specific antibody over its ratio to labeled reference immunoglobulin in non-target areas. These values may be used to generate a related output signal, advantageously a gradation of colors on a color television screen. The photoscanning device may also include computed tomographic capabilities. The combination of this highly efficient subtraction technique with the use of highly monospecific, preferably monoclonal antibodies labeled to give the maximum balance between high activity and acceptable immunospecificity provides a tumor localization and detection method of significantly improved resolution.

Further improved resolution can be achieved using a technique reported by Goldenberg, et al., *Proc. Nat. Acad. Sci. USA,* 78, 7754 (1981). These authors used Tc-99m-pertechnetate and Tc-99m-labeled human serum albumin as reference substances which were injected prior to each scan, and I-131-labeled specific antibody. They further refined the subtraction method for certain organs, such as liver, by use of an organ-specific radionuclide (e.g., Tc-99m-sulfur colloid), whereby the organ's image was selectively extracted from the region of interest, and then the Tc-99m radioactivity was subtracted, pixel by pixel, from that of I-131. The organ-specific radionuclide was given following the routine examination with Tc-99m-human serum albumin and Tc-99m-pertechnetate as non-target subtraction agents. In other instances, such as for the lungs, selective organ extraction was accomplished by outlining the organ of concern electronically, and then processing according to the standard subtraction method. By this means, greater confidence in identifying tumor-related radioactivity (as compared to non-target background) was achieved.

The antibodies of the invention are advantageously administered in the form of injectable compositions. For general screening, and for many types of localization and therapy, injection will be intravenous, intraarterial or intrathecal. The injectable antibody fragment solution will be administered into a vein, artery or into the spinal fluid over the course of from 2 minutes to about 45 minutes, preferably from 10 minutes to 20 minutes. In certain cases, intradermal or intracavitary administration is advantageous. Where the tumor is supplied by a known artery, intraarterial administration is preferred for therapy. In addition, intrathecal administration may be used for tumors located in the brain. Intradermal and intracavitary administration are advantageous for tumors restricted to areas close to particular regions of the skin and/or to particular body cavities.

A typical injectable composition according to the invention contains about 10 mg human serum albumin (1% USP:Parke-Davis) and from about 20 to 200 micrograms of radiolabeled specific antibody per milliliter of 0.01M phosphate buffer (pH 7.5: Bioware) containing 0.9% NaCl. Where the subtraction technique of the invention is used, a quantity of radiolabeled normal immunoglobulin roughly equal to the weight of specific antibody is also included. Other conventional pharmaceutically acceptable injection vehicles may be used where indicated, such as for intrathecal, intradermal or intracavitary injection as well as for intravenous or intraarterial injection.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Antibodies used in these examples are highly specific, either prepared by conventional immunization followed by complement inactivation, adsorption to remove hemagglutination components and affinity purification against cross-reactive antigens and the specific antigen, or hybridoma-derived monoclonal antibodies.

EXAMPLE 1

Preparation of labeled indifferent IgG (a) Myeloma IgG derived from MOPC-21 murine myeloma, commercially available from, e.g., Litton Bionetics, is labeled with technetium-99m according to the procedure of Wong et al., *Int. J. Appl. Rad. Isot.,* 29, 251 (1978). A 60 mCi sample of sodium Tc-99m-pertechnetate is reduced by addition of 0.5 ml of a solution of 0.1 mg $SnCl_2$ in 0.05N HCl solution. The mixture (pH 1.8) is incubated at room temperature for 10 min, then readjusted to pH 7.4 with 0.75 ml trisodium citrate/NaOH solution (pH 12.4). Then, 1 ml of a solution containing 4 mg of the myeloma IgG in Sorenson phosphate buffer (pH 7.4) is added by very slow injection with gentle swirling into the reaction vial, and incubated for 30 min at room temperature. The radionuclide is incorporated into the protein to the extent of about 98%, as shown by protein electrophoresis, and there is no appreciable reduction of the integrity of the indifferent immunoglobulin.

(b) The myeloma IgG from MOPC-21 murine myeloma, at a concentration of 5 mg/ml, is treated with a 250-fold molar excess of the carboxycarbonic anhydride of diethylenetriaminepentaacetic acid (DTPA) at a concentration of 0.025 mM, in 100 mM bicarbonate at pH 7.5. The anhydride is prepared by the method of Krejcarek et al., *Biochem. Biophys. Res. Commun.,* 77, 581 (1977). After extensive dialysis against metal-free NaCl, the DTPA-treated protein, at a concentration of 2 mg/ml, is labeled with 1 mCi indium-111, as $InCl_3$, in 50 mM citrate at pH 3.6. Free In-111 is removed by ion-exchange chromatography, followed by dialysis against buffered NaCl at pH 6.6, according to the procedure of Scheinberg et al., *Science,* 215, 1511 (1982).

EXAMPLE 2

Quality control procedures for radiolabeled antibodies against intracellular tumor-associated antigens (a) Gel filtration chromatography on Sephacryl S-300

1. The labeled antibody against an intracellular tumor-associated antigen is diluted 1:1000 in PBS, pH 7.2, containing 0.5% human serum albumin (HSA).

2. An aliquot of 400 μl (containing about 16.7 ng protein) of the diluted labeled antibody is added to 1.6 ml PBS, pH 7.2, containing 5 mg indifferent IgG (preferably of the same species as the antibody) which acts as a "carrier" protein, and applied to a 2.6×100-cm column of Sephacryl S-300 that has been equilibrated with PBS, pH 7.2, containing 0.02% sodium azide.

3. The column is eluted with the same buffer, at a flow rate of 50 ml/hr, and fractions of 5.0 ml are collected.

4. The optical density at a wavelength of 280 nm of the column eluents is monitored and recorded. The recorder is equipped with an event-marker which marks the recorded absorbance corresponding with the appropriate fractions.

5. A total of about 130 fractions are collected and the radionuclide content (cpm) in each one is determined by means of a gamma scintillation counter.

6. The chromatographic distribution pattern of the labeled antibody is compared to that of the "carrier" indifferent, unlabeled IgG by plotting the cpm content in each fraction on the chart of the absorbance at 280 nm values.

This procedure allows a determination of the amount of radionuclide conjugated to the antibody IgG. A determination can also be made by electrophoresis of the sample, compared to electrophoresis of the unlabeled immunoglobulin.

(b) Affinity-chromatography on the appropriate antigen-immunoadsorbent

1. The appropriate antigen adsorbent, made by coupling the antigen extract to which the antibody is reactive, e.g., HCG, AFP, CSAp and the like, to Sepharose 4B by the cyanogen bromide method, as described in Example 2(b) of U.S. Ser. No. 126,261 for CSAp affinity chromatography, which has the capacity to bind more than 10 ng antibody, is packed into a 10 ml plastic syringe equipped with a porous disc at the bottom. Another disc is fitted on the top of the immunoadsorbent gel, and a valve is installed on the outlet of the minicolumn.

2. The immunoadsorbent is equilibrated with 0.1M sodium phosphate, pH 7.0, containing 1% indifferent serum of the species of the antibody (e.g., mouse) and 0.02% sodium azide.

3. A volume of 200 μl of the 1:1000 dilution of the labeled antibody is applied to the column and washed into the immunoadsorbent with addition of 200 μl of the phosphate buffer.

4. The flow is stopped and the antibody is allowed to react with the immunoadsorbent for 30 min at room temperature.

5. At the end of this incubation period the column is eluted with 10 ml of the phosphate buffer, and the eluent is collected in a 16×150-mm test tube, and this is designated as Fraction #1.

6. Subsequently the column is eluted with 10 ml 6M guanidine hydrochloride made in sodium phosphate, pH 7.0, and the eluent is collected in a second 16×150-mm test tube, designated as Fraction #2.

7. The column is then washed with 10 ml of the initial phosphate buffer and the eluent is collected in a third 16×150-mm test tube, designated Fraction #3.

8. A reference sample is prepared by diluting 200 μl of the diluted labeled antibody to a final volume of 10 ml with the phosphate buffer, designated as "Total Counts Applied" to the immunoadsorbent.

9. The cpm content in each of the three fractions and reference tube is determined.

10. The following calculations are made:

% Recovery:

i.

$$\frac{[cpm \text{ Fraction } \#1] + [cpm \text{ Fractions } \#2 \text{ and } \#3]}{\text{"Total Counts Applied"}} \times 100$$

% Non-reactive IgG:

ii.

$$\frac{cpm \text{ Fraction } \#1}{[cpm \text{ Fraction } \#1] + [cpm \text{ Fractions } \#2 \text{ and } \#3]} \times 100$$

% Immunoreactive IgG:

iii.

$$\frac{[cmp \text{ Fractions } \#2 \text{ and } \#3]}{[cpm \text{ Fraction } \#1] + [cpm \text{ Fractions } \#2 \text{ and } \#3]} \times 100$$

(c) Solid-phase radioassay

The immunoreactivity of the labeled antibody can also be determined by a solid-phase radioassay, using intracellular tumor-associated antigens. Five μl (in 50 μl) of the antigen solutions are added to each well of 96-well microtiter polyvinyl plates and left to dry. The microtiter wells are treated with 100 μl of 5% bovine serum albumin (BSA) in PBS and incubated for 1 hr at 37° C., in order to reduce nonspecific protein absorption. The BSA is removed and varying amounts of the radiolabeled antibody (in 50 μl) are added. After incubation for 1 hr at 37° C., the unbound immunoglobulin is removed by washing the plates with 1% BSA in PBS. The plates are incubated for an additional hour and then washed extensively with 1% BSA in PBS. The bound counts are then detected by cutting the individual wells from the plate and measuring the radioactivity in a gamma scintillation counter. These results are then compared to identical plates in which an identically labeled indifferent immunoglobulin of the same species (e.g., mouse serum IgG or MOPC-21 IgG) is used instead of the specific antibody, thus allowing a determination of the % of a radiolabeled antibody immunoreactive with the intracellular tumor-associated antigen of interest.

(d) Tumor localization in vivo in human tumor xenografts

Athymic, nude mice (nu/nu on a Balb/c background) are grafted subcutaneously with a suitable number (e.g., $2 \times 10^6$) of human cancer cells of the type desired for radiolabeled antibody localization. The mice can also be grafted with control, different human cancer cells lacking the appropriate intracellular antigen, in order to demonstrate selective antibody localization only in the suitable, intracellular-antigen-containing human tumors. The radiolabeled antibody or indifferent immunoglobulin (2 to 80 μg) is injected intracardially or intraperitoneally after tumors are established, usually when these measure 0.4–1.0 cm in diameter. When a radioiodine label is used, the drinking water is supplemented with 0.1% v/v NaI throughout the experiments, commencing about 2 days before injection of the radioiodinated antibody or indifferent IgG. One to five days later (depending on radionuclides used), the mice are sacrificed and dissected, the tumors, visceral organs, muscle, bone, blood samples and residual carcass are weighed and assayed for radioactivity by a gamma scintillation counter. In order to assess specific uptake of the radiolabeled antibody in the tumor, a similar quantity of indifferent IgG of the same or a different species, or, preferably, the myeloma MOPC-21 IgG in the case of murine monoclonal antibodies, is labeled with an isotope of different energy and capable of separation from that of the isotope used to label the specific antibody (e.g., I-131 for antibody and I-125 for indifferent IgG; I-131 for antibody and Tc-99m for indifferent IgG), and injected simultaneously in equivalent amounts of IgG protein with the specific radiolabeled antibody preparation. After weighing the organs and assaying for radioactivity, the results are expressed as a percentage of injected radioactivity/g tissue and/or as a ratio of injected radioactivity/g tumor to that of a particular reference tissue or to blood (tumor/nontumor and tumor/blood ratios). When the mice receive dual labeled immunoglobulins and antibody simultaneously, a "localization ratio" is calculated for each organ by the formula, $$\frac{\text{tissue:blood ratio labeled antibody}}{\text{tissue:blood ratio indifferent immunoglobulin}}$$

This procedure will show preferential uptake of labeled specific antibody in the tumor and substantially the same uptake of specific and indifferent IgG in normal organs.

(e) In vivo kinetics and distribution of dual labeled antibody and indifferent immunoglobulin preparations injected simultaneously.

The similarity in kinetics, metabolism, and organ distribution of antibody and indifferent immunoglobulin, each labeled with a different isotope capable of detection and discrimination from one another by a gamma camera, for the time period of imaging, preferably within 24 hours but, with certain radionuclide combinations, up to at least 48 hours, can be evaluated prior to clinical studies by similar procedures to those described in part (d). However, it is advantageous that the mice (or another animal species) not bear the appropriate tumor, or bear another control tumor which should not accrete the antibody or indifferent immunoglobulin significantly. The mice are then sacrificed at regular intervals (e.g., every 4-8 hours) during a 24-48 hr period and the organs dissected and weighed, and assayed for radioactivity, as described in part (d). The percentage of injected radioactivity/g tissue and the tissue:blood ratio for the two radiolabeled preparations should be virtually equal or, in the formula of part (d), almost 1, as long as the kinetics and distribution of the antibody and indifferent immunoglobulin preparations labeled with two different radionuclides are essentially identical for the time period desired for imaging experiments.

EXAMPLE 3

Quality control procedure for radiolabeled indifferent IgG (a) Gel filtration chromatography on Sephacryl S-300

The procedure of Example 2(a) is followed, except that indifferent IgG is used instead of antigen-specific IgG.

(b) Affinity-chromatography on the appropriate antigen-immunoadsorbent

The procedure of Example 2(b) is followed, with the exception that the immunoadsorbent is made of antibody against the species IgG of the indifferent immunoglobulin, such as goat anti-mouse IgG for the indifferent murine IgG or donkey anti-goat IgG for indifferent goat IgG, coupled to Sepharose 4B.

EXAMPLE 4

Preparation of injectable compositions

Sterile, pyrogen-free solutions are prepared as shown.

(a) A sterile solution containing, per ml:
(1) 34 mg Human Serum Albumin (HSA) (1%, USP, Parke-Davis)
(2) 0.04M phosphate buffer, pH 7.4 (Bioware)
(3) 0.9% NaCl
(4) 10 μg I-131-anti-HCG prepared according Example 1 of U.S. Ser. No. 126,621 having an average of about 5 atoms of iodine/molecule, and a specific activity of 20–40 Ci/g IgG protein.

The labeled antibody is stored in a solution of (1), (2) and (3) at a concentration of 20 μg/ml and diluted with an equal volume of 1% HSA in PBS to prepare this solution.

(b) A sterile solution according to the procedure of part (a) except that the antibody is the I-131-anti-AFP IgG (monoclonal) prepared according to Example 3 of U.S. Ser. No. 126,621, stored in 1% HSA in PBS at a concentration of 20 μg/ml and having comparable activity.

(c) A sterile solution according to the procedure of part (a) except that the antibody is the radiolabeled, boron-conjugated anti-AFP IgG prepared according to Example 5 of U.S. Ser. No. 126,621, stored in 1% HSA in PBS at a concentration of 20 μg/ml and having comparable activity.

(d) A sterile solution according to the procedure of part (a) except that the antibody is replaced by the technetium-99m-labeled indifferent IgG prepared in Example 3 (a), stored in 1% HSA in PBS at a concentration of 20 μg/ml and having comparable activity.

EXAMPLE 5

Tumor Localization (a) Localization of testicular and hepatic cancers are effected according to the procedure of Example 7 (b) of U.S. Ser. No. 126,261, except that the antibody solution is a solution according to Example 4(a) or 4(b) above, and an equal volume of the Tc-99m-labeled indifferent IgG according to Example 4(d) above is used instead of I-123-labeled IgG.

(b) Imaging is comparable to that in Example 7(b) of U.S. Ser. No. 126,621, but use of Tc-99m for subtraction is more convenient than I-123, which is less accessible to nuclear medicine laboratories.

EXAMPLE 6

Tumor Therapy (a) Neutron irradiation of a localized hepatic tumor is effected according to the procedure of Example 8 (b) of U.S. Ser. No. 126,261, except that the tumor is localized using the Tc-99m-labeled IgG and the subtraction procedure of Example 5 above and the radiolabeled, boron-conjugated antibody is the antibody prepared according to Example 4 (c) above. Comparable results with the attendant added convenience noted above are achieved.

The preceding examples can be repeated with similar success by substituting the generically or specifically described reactants and/or operating conditions of this invention for those used in the preceding examples. For example, the anti-AFP antibody can be labeled with Tc-99m or In-111 analogously to the procedures for labeling indifferent IgG of Example 1 above and the indifferent IgG can be labeled with I-131. Other variants disclosed generally hereinabove can also be used with comparable efficacy.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for detecting and localizing a tumor which either produces or is associated with an intracellular marker substance, which comprises injecting a human subject parenterally with an antibody specific to said marker substance and radiolabeled with a pharmacologically inert radioisotope capable of detection using a photoscanning device, and with indifferent immunoglobulin from the same or different species as that used to prepare said specific antibody, said indifferent immunoglobulin being radiolabeled with a pharmacologically inert radioisotope of a different element from that used to label the specific antibody and emitting at an energy capable of independent detection using said photoscanning device, the radiolabeling be so effected that the kinetics and distribution of the radiolabeled specific antibody and indifferent immunoglobulin in said subject are substantially the same during the time period required for scanning; and scanning the subject with said photoscanning device, the level of activity of the labeled indifferent immunoglobulin being used to determine the distribution of background activity due to non-targeted specific antibody, said background activity being subtracted from the total activity of specific antibody, whereby the activity of substantially only the targeted tumor-localized specific antibody is determined and said tumor is thereby detected and localized.

2. The method of claim 1, wherein the specific antibody is radiolabeled with one of, and the indifferent immunoglobulin is labeled with another of Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-197, Mercury-203, Rhenium-99m, Rhenium-105, Rhenium-101, Scandium-47, Tellurium-121m, Tellurium-122m, Tellurium-125m, Thulium-165, Thulium-167, Thulium-168, Technetium-99m or Fluorine-18.

3. The method of claim 1, wherein the specific antibody is radiolabeled with one of I-131, Ga-67, Tc-99m or In-111 and the indifferent immunoglobulin is radiolabeled with another of I-131, Ga-67, Tc-99m or In-111.

4. The method of claim 1, wherein tumor localization is effected within 48 hours of injection of the labeled immunoglobulins.

5. The method of claim 4, wherein localization is effected within 24 hours of injection.

6. The method of claim 1, wherein the specific antibody is specific to human chorionic gonadotropin (HCG) or its beta-subunit, alpha fetoprotein (AFP) or colon-specific antigen-p (CSAp).

7. A method of tumor radiotherapy, which comprises parenterally injecting into a human subject having a tumor which produces or is associated with an intracellular marker substance a radiotherapeutically effective amount of an antibody which is specific to said marker substance and radiolabeled with a pharmacologically inert radioisotope capable of detection with a photoscanning device, said labeled antibody further containing in chemical combination at least one addend containing at least five atoms of boron with at least a natural abundance of Boron-10 isotope; injecting into said subject indifferent immunoglobulin from the same or different species as that used to prepare said specific antibody, said indifferent immunoglobulin being radiolabeled with a pharmacologically inert radioisotope of a different element from that used to label the specific antibody and emitting at an energy capable of independent detection using said photoscanning device, the radiolabeling being so effected that the kinetics and distribution of the radiolabeled specific antibody and indifferent immunoglobulin in said subject are substantially the same during the time period required for scanning; localizing the tumor by scanning the subject with said photoscanning device, the level of activity of the labeled indifferent immunoglobulin being used to determine the distribution of background activity due to non-targeted specific antibody, said background activity being subtracted from the total activity of specific antibody, whereby the activity of substantially only the targeted tumor-localized specific antibody is determined and said tumor is thereby detected and localized; and directing a beam of thermal neutrons at said tumor location.

8. The method of claim 7, wherein the specific antibody is specific to human chorionic gonadotropin (HCG) or its beta-subunit, alpha fetoprotein (AFP) or colon-specific antigen-p (CSAp).

9. An injectable composition, which comprises
   (a) a substantially monospecific antibody having a specific immunoreactivity of at least 70% to an intracellular marker substance produced by or associated with a tumor and a cross-reactivity to non-tumor associated antigens of less than 15%; said antibody being radiolabeled with a pharmacologically inert radioisotope capable of detection with a photoscanning device, said labeling being effected to an extent sufficient to reduce the specific immunoreactivity of the antibody by from 5 to 33%;
   (b) indifferent immunoglobulin from the same or different species as that used to prepare said specific antibody, said indifferent immunoglobulin being radiolabeled with a pharmacologically inert radioisotope of a different element from that used to label the specific antibody and emitting at an energy capable of independent detection by said photoscanning device; and
   (c) a pharmaceutically acceptable injection vehicle.

10. The composition of claim 9, wherein the specific antibody is specific to human chorionic gonadotropin (HCG) or its beta-subunit, alpha fetoprotein (AFP) or colon-specific antigen-p (CSAp).

11. The composition of claim 9, wherein the specific antibody is labeled with one of I-131, Ga-67, Tc-99m or In-111, and the indifferent immunoglobulin is labeled with another of I-131, Ga-67, Tc-99m or In-111.

12. The method of claim 1, wherein the radioisotopes used to label the specific antibody and the indifferent immunoglobulin both emit in the 10–5,000 kev range.

13. The method of claim 12, wherein said range is 100–500 kev.

14. The method of claim 7, wherein the radioisotopes used to label the specific antibody and the indifferent immunoglobulin both emit in the 10–5,000 kev range.

15. The method of claim 14, wherein said range is 100–500 kev.

16. The composition of claim 9, wherein the radioisotopes used to label the specific antibody and the indifferent immunoglobulin both emit in the 10–5,000 kev range.

17. The method of claim 16, wherein said range is 100–500 kev.

* * * * *